United States Patent [19]

Sahatjian

[11] Patent Number: 5,599,298
[45] Date of Patent: Feb. 4, 1997

[54] BODILY SAMPLE COLLECTION BALLOON CATHETER METHOD

[75] Inventor: Ronald A. Sahatjian, Lexington, Mass.

[73] Assignee: Boston Scientific Corporation, Natick, Mass.

[21] Appl. No.: 175,791

[22] Filed: Dec. 30, 1993

[51] Int. Cl.$^6$ .......................... A61M 31/00; A61B 10/00
[52] U.S. Cl. ........................ 604/49; 128/749; 128/759; 128/760; 604/96; 606/194
[58] Field of Search ............................ 604/49,52,53–55, 604/265, 96; 128/898, 749, 752, 758, 759, 760, 763, 765, 756, 757; 606/159, 160, 194

[56] References Cited

U.S. PATENT DOCUMENTS

| | | |
|---|---|---|
| 2,701,559 | 2/1955 | Cooper . |
| 3,577,981 | 5/1971 | Kuris . |
| 3,699,956 | 10/1972 | Kitrilakis et al. . |
| 3,777,743 | 12/1973 | Binard et al. . |
| 3,996,935 | 12/1976 | Banko . |
| 4,172,446 | 10/1979 | Bucalo ................................ 128/769 |
| 4,299,226 | 11/1981 | Banka . |
| 4,364,392 | 12/1982 | Strother et al. . |
| 4,403,612 | 9/1983 | Fogarty . |
| 4,423,725 | 1/1984 | Baran et al. . |
| 4,643,192 | 2/1987 | Fiddian-Green . |
| 4,735,214 | 4/1988 | Berman ................................ 128/759 |
| 4,763,670 | 8/1988 | Manzo . |
| 4,766,907 | 8/1988 | de Groot et al. . |
| 4,773,901 | 9/1988 | Norton ................................ 604/265 |
| 4,820,270 | 4/1989 | Hardcastle et al. . |
| 4,832,034 | 5/1989 | Pizziconi et al. . |
| 4,875,486 | 10/1989 | Rapoport et al. . |
| 4,876,126 | 10/1989 | Takemura et al. . |
| 4,958,625 | 9/1990 | Bates et al. . |
| 4,994,033 | 2/1991 | Shockey et al. .................... 604/101 |
| 5,006,526 | 4/1991 | Meier et al. . |
| 5,026,607 | 6/1991 | Kiezulas . |
| 5,049,132 | 9/1991 | Shaffer et al. ..................... 604/101 |
| 5,091,205 | 2/1992 | Fan . |
| 5,120,322 | 6/1992 | Davis et al. ....................... 604/265 |

(List continued on next page.)

FOREIGN PATENT DOCUMENTS

| | | |
|---|---|---|
| 0166998 | 1/1986 | European Pat. Off. . |
| 0372088 | 6/1990 | European Pat. Off. . |
| 0399712 | 11/1990 | European Pat. Off. . |
| 3519626 | 12/1986 | Germany ........................ 606/159 |
| 54-35036 | 10/1979 | Japan . |
| 1069826 | 9/1982 | U.S.S.R. . |
| 2112646 | 7/1983 | United Kingdom . |
| 88/06861 | 9/1988 | WIPO . |
| 91/08790 | 6/1991 | WIPO . |
| 92/08515 | 5/1992 | WIPO . |
| 92/11895 | 7/1992 | WIPO . |
| 93/07806 | 4/1993 | WIPO . |
| 93/11751 | 6/1993 | WIPO . |

OTHER PUBLICATIONS

Wolinsky et al., "Local Introduction of Drugs into the Arterial Wall: A Percutaneous Catheter Technique", *Journal of Interventional Cardiology*, vol. 2, No. 4, 1989, pp. 219–228.

Waller et al., "Vessel Wall Pathology After Angioplasty", *Cardio*, Aug., 1990, pp. 57, 70–72, 81.

*Primary Examiner*—Randall L. Green
*Assistant Examiner*—Ronald K. Stright, Jr.
*Attorney, Agent, or Firm*—Fish & Richardson P.C.

[57] ABSTRACT

Treating a patient by collecting a bodily sample from deep within the body of a patient and collecting the sample outside the body to facilitate treatment of the patient. A sampling probe is provided in the form of an elongate catheter having a proximal portion that remains outside the body and a distal portion that can be located within the body. The distal portion includes a polymer on its outer surface capable of receiving a substantial amount of bodily sample. The catheter is positioned within the body and the sample is taken by exposing the polymer by placing it in proximity within a desired location so that said bodily sample is received by the polymer. The catheter is removed from the patient and the sample is collected outside the body.

25 Claims, 3 Drawing Sheets

U.S. PATENT DOCUMENTS

| | | | |
|---|---|---|---|
| 5,135,516 | 8/1992 | Sahatjian et al. | 604/265 |
| 5,180,366 | 1/1993 | Woods | 604/96 |
| 5,186,172 | 2/1993 | Fiddian-Green . | |
| 5,197,470 | 3/1993 | Helfer et al. . | |
| 5,213,576 | 5/1993 | Abiuso et al. | 604/96 |
| 5,213,577 | 5/1993 | Kratzer | 604/101 |
| 5,213,580 | 5/1993 | Slepian et al. | 623/1 |
| 5,217,456 | 6/1993 | Narciso, Jr. | 606/15 |
| 5,232,444 | 8/1993 | Just et al. | 604/96 |
| 5,238,002 | 8/1993 | Devlin et al. . | |
| 5,254,089 | 10/1993 | Wang | 604/96 |
| 5,304,121 | 4/1994 | Sahatjian . | |

BODILY SAMPLE COLLECTION BALLOON CATHETER METHOD

FIELD OF THE INVENTION

The invention relates to collecting bodily samples from a patient.

BACKGROUND OF THE INVENTION

Samples of tissue, bodily fluids, etc. are frequently taken from patients for analysis to help in diagnosing disease or monitoring the progress of treatment. For example, samples of cells from the lungs or gastrointestinal tract are taken with a cytology brush. The brush is rubbed against tissue to scrape cells from the surface and collect them in the bristles. Other sampling techniques sever tissue from the body. For example, biopsies are taken with a needle device that penetrates the tissue and then severs a sample with a sharp cutting cannula. A biopsy forceps device is another example. This device is a catheter with a jaw-type cutter at its end. The catheter is threaded through an endoscope to a position deep within the body where it bites a sample of tissue from a desired location. Samples of tissue are taken from within blood vessels using an artherectomy cutter. An artherectomy cutter is a catheter that can be threaded through a blood vessel to a desired site. A cutting member is provided at the end of the catheter. The cutting member can be pressed against a desired site in the blood vessel, such as the site of a vascular occlusion resulting from the build up of plaque, and then actuated to sever occluding matter from the wall of the blood vessel. Samples of bodily fluids are typically drawn from body conduits.

SUMMARY OF THE INVENTION

In a first aspect, the invention features a method for taking a bodily sample from a blood vessel of a patient and collecting the sample outside the body. The method includes providing a sampling probe in a form of an elongate vascular catheter having a proximal portion that remains outside the body and a distal portion that can be located in the blood vessel. The distal portion includes an expandable member that can be selectively expanded to larger diameters and contracted to smaller diameters. The expandable portion has a polymer on its outer surface that is capable of receiving a substantial amount of bodily sample. The method also includes positioning the expandable portion at the desired location within the blood vessel and collecting the sample by exposing the polymer by expanding the expandable portion sufficient to place the polymer in proximity with the wall of the blood vessel so that a bodily sample is received by the polymer. The method also includes contracting the expandable portion to smaller diameters so that the polymer does not contact the wall of the blood vessel, removing the catheter from the patient, and collecting the sample outside the body.

Embodiments may also include one or more of the following features. The polymer is a hydrogel. The sample is removed from the polymer prior to analyzing. The sample is removed by flushing the polymer with aqueous solution. The method includes expanding the expandable portion to contact the vessel wall with the polymer with sufficient force to compress the polymer to a reduced thickness and contracting the expandable portion to re-expand the polymer and draw the sample to the polymer by suction forces created by the re-expansion. The method includes moving the catheter axially while the polymer is in contact with the wall of the vessel to brush the polymer along the wall to collect the sample. The method includes introducing the catheter into the blood vessel while the hydrogel is in a substantially nonswelled state and collecting the sample by absorption into the hydrogel as the hydrogel swells during exposure. The method includes providing a sheath that can be positioned over the expandable portion to limit exposure of the hydrogel prior to positioning at the desired location and exposing the expandable portion from the sheath after positioning at the desired location. The method includes providing a sheath that can be positioned over the expandable portion after collecting the sample to reduce exposure of the hydrogel while removing the catheter from the patient. The method includes providing a probe in the form of an angioplasty catheter having an expandable portion in the form of an inflatable balloon; the coating is a hydrogel disposed over the balloon. The method includes positioning the expandable portion adjacent an occlusion in the vessel and simultaneously expanding the occlusion and collecting the sample by expanding the expandable portion. The method includes performing angioplasty on an occluded region of the blood vessel, positioning the expandable portion adjacent the occluded region after the angioplasty, and collecting the sample from the region. The polymer includes a probe for preferential binding a target component. The method includes analyzing the sample to determine the likelihood of restenosis of the region, analyzing the sample to determine cellular proliferation, analyzing the bodily fluid in the sample for biological indicators, analyzing cells in the sample, analyzing the sample to determine the structural composition of material creating an occlusion such as the level of calcification, cholesterol, or fibrous tissue. The method includes selecting a treatment for the occlusion based on the analysis. The method includes taking cells from the body and placing them back in the body.

In a particular aspect, the invention features a method for treating a patient by collecting a sample indicative of physiological function from the body of the patient and analyzing the sample to determine physiological function. The method includes providing a sampling probe with a hydrogel polymer. The hydrogel is composed of a porous cross-linked polymer matrix having the ability to receive substantial amounts of bodily sample. The hydrogel is exposed to the body of a patient so that a bodily sample is received by the hydrogel. The hydrogel is then removed from the patient. The sample is analyzed to determine physiological function.

In embodiments, the method may include compressing the hydrogel against a surface of the body and expanding the hydrogel to draw the sample to the hydrogel by suction forces created by the expansion. The method may include placing the hydrogel in contact with a surface of the body and moving the hydrogel across the surface to brush the hydrogel along the surface to collect the sample. The method may include exposing the hydrogel while the hydrogel is in a substantially non-swelled state, and collecting the sample by absorption as the hydrogel swells during the exposure.

In another aspect, the invention features a kit for treating a patient by collecting a sample from the blood vessel of a patient that can be analyzed to determine physiological function. The kit includes a sampling probe in the form of an elongate vascular catheter having a proximal portion that remains outside the body and a distal portion that can be located in the blood vessel. The distal portion includes an expandable member that can be selectively expanded to larger diameters and contracted to smaller diameter. The expandable portion includes a swellable hydrogel polymer composed of a cross-linked polymer matrix capable of receiving substantial amounts of bodily sample. The kit also includes apparatus for facilitating analysis of the sample to determine physiological function.

Embodiments may include one or more of the following features. The hydrogel is a polyacrylic acid hydrogel having a thickness of about 10–50 μm in the swelled state. The hydrogel includes a probe for preferentially binding a target component. The kit includes a protective sheath for protecting the hydrogel from substantial exposure to the vessel prior to and after receiving the sample. The vascular catheter is a balloon dilitation catheter.

In another aspect, the invention features treating a patient by taking a bodily sample from deep within the body of a patient and collecting the sample outside the body to facilitate treatment of the patient. A sampling probe is provided in the form of an elongate catheter having a proximal portion that remains outside the body and a distal portion that can be located within the body. The distal portion includes a polymer on its outer surface capable of receiving a substantial amount of bodily sample. The catheter is positioned within the body, and the sample is taken by exposing the polymer by placing it in proximity with a desired location so that the bodily sample is received by the polymer. The catheter is removed from the patient and the sample is collected outside the body. Preferably, the polymer is a hydrogel.

The invention has many advantages. In embodiments, a bodily sample, e.g., of tissue or of bodily fluid containing cells or chemical indicators of biological function, can be collected from a specific, local site within a blood vessel in a low stress manner by bringing a polymer that is capable of receiving the sample in proximity to the desired site. In embodiments, the polymer is a sponge-like polymer which is compressed initially and then reexpanded to create a suction force that draws the bodily sample into the polymer. A swellable polymer can be used by delivering it in a non-swelled state to the site and then allowing it to swell with bodily sample material. In these, as well as other examples discussed below, the sample is taken without mechanically disturbing the wall of the blood vessel to an excessive extent. This is an advantage since mechanically disturbing the vessel can cause further injury by inducing intimal proliferation (excessive scar forming) or dislodging portions of the occluding material from the vessel wall so that they enter the bloodstream.

Other features and advantages follow.

DESCRIPTION OF THE EMBODIMENTS

Figure 1:
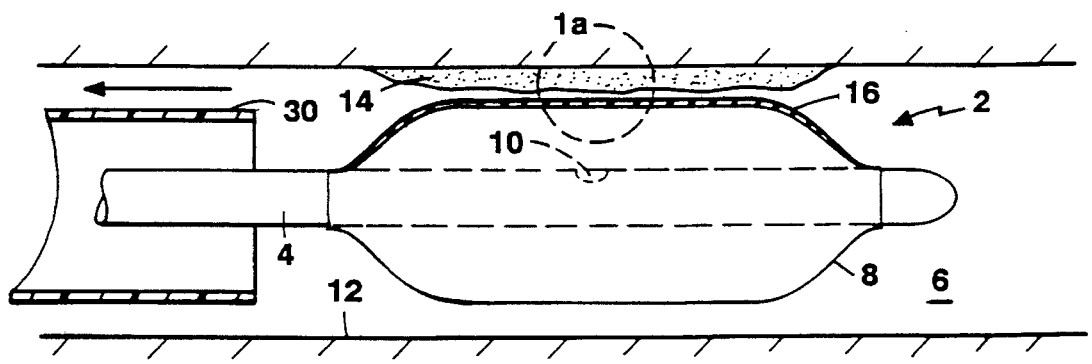
FIGS. 1–6 illustrate the structure and one use of an embodiment of the invention.

Referring to FIG. 1, a sample collection apparatus 2 includes a catheter 4 that is constructed to be threaded through a lumen 6 of a blood vessel. The catheter 4 includes near its distal end an expandable portion, which may be, for example, a balloon 8. The balloon is inflated and deflated by injecting or withdrawing fluid through the catheter which exits a port 10 located within the balloon. The apparatus may include a protective sheath 30 that extends over the balloon while it is threaded into and out of the body. The balloon can be exposed from the sheath once the site is reached. The sheath may be an introducer catheter of the type used to direct angioplasty catheters into the coronary arteries.

In FIG. 1, the balloon is in a partially inflated state, less than its full inflated diameter, such that it does not contact the wall 12 of the blood vessel. The catheter has been positioned such that the balloon is adjacent a portion 14 of the vessel wall 12 that is diseased. For example, the portion 14 may be an occlusion caused by the build-up of plaque or the growth of smooth muscle cells, a condition known as intimal proliferation. The portion of the vessel may have already been treated by balloon catheter angioplasty so that the lumen is substantially open.

Figure 1A:
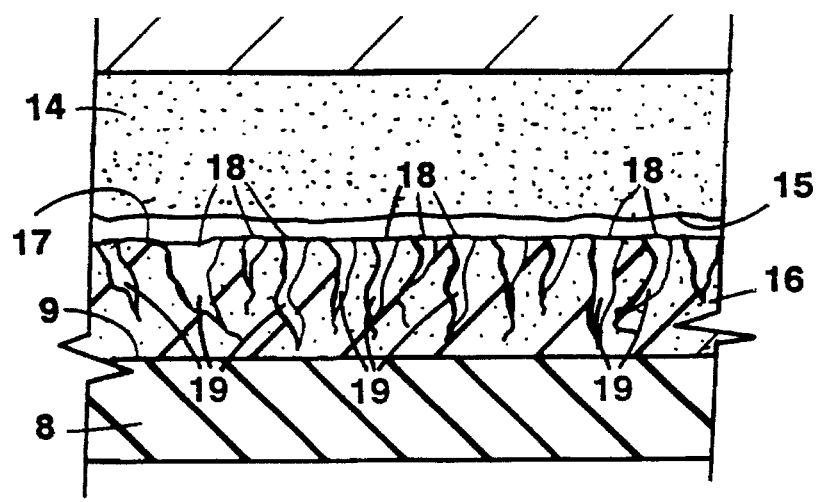

Referring as well to FIG. 1a, which is a greatly enlarged view of the area in the circle in FIG. 1, the balloon 8 includes a sponge-like polymer coating 16 on at least a portion of its outer surface 9. The coating 16 has a substantial thickness and includes pore openings 18 on its outer surface 17 that allow access to spaces 19 within the bulk of the coating 16.

Figure 2:
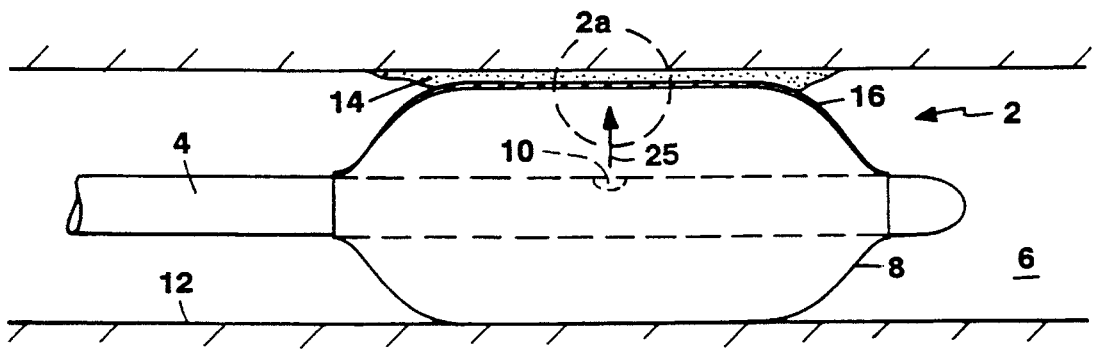
Figure 2A:
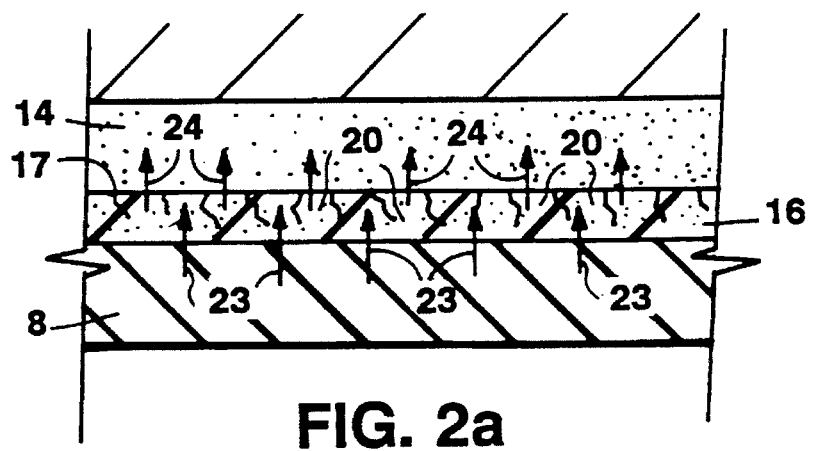

Referring to FIGS. 2 and 2a, the balloon 8 is further inflated by the introducing additional inflation fluid (arrow 25), which causes the coating 16 to physically contact the portion 14 of the vessel. The balloon is expanded sufficiently to compress (arrows 23) the coating 16 between the balloon 8 and the wall portion 14, but generally not such that the portion 14 of the wall is damaged or physically disturbed to an excessive extent. As the coating 16 is compressed, the outer surface 17 of the coating is placed in intimate physical contact with the exposed surface 15 of the portion 14 of the wall of the lumen. Further, the compression causes the spaces in the coating 16 to collapse.

Figure 3:
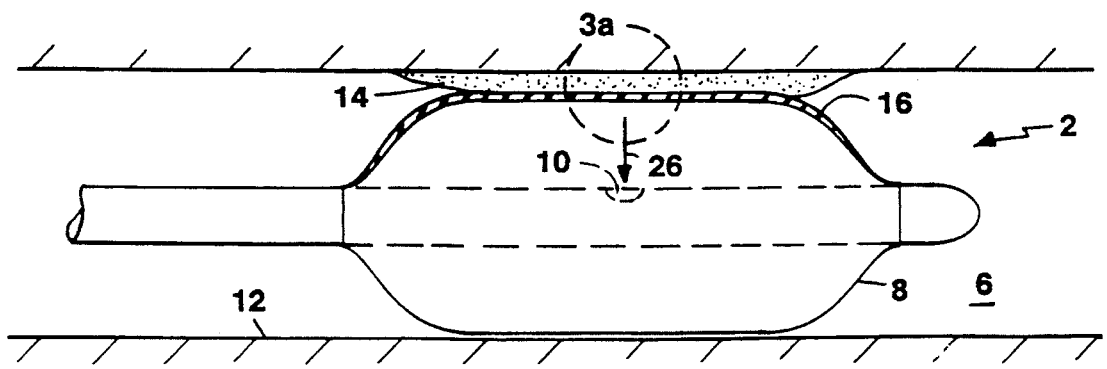
Figure 3A:
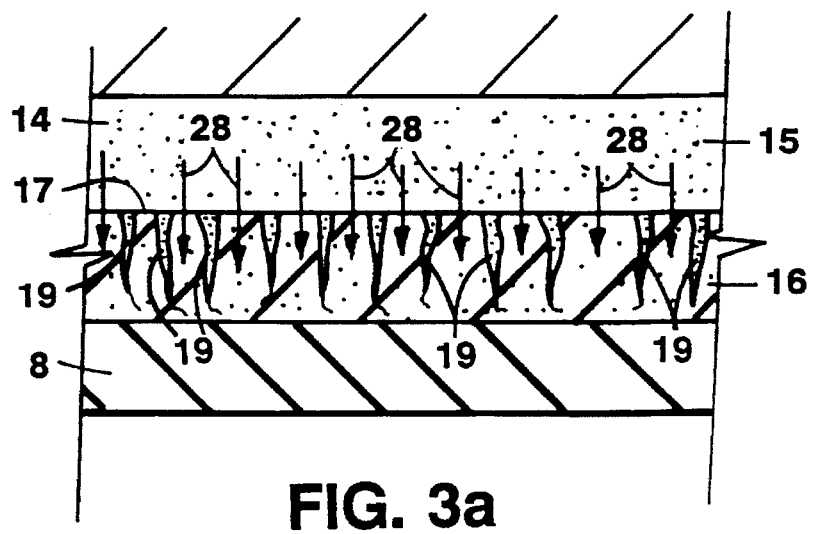

Referring to FIGS. 3 and 3a, the balloon is then partially deflated by withdrawing inflation fluid (arrow 26) through the port 10 of the catheter. The compression force on the coating 16 is thus released, which causes the coating to reexpand, opening the spaces 19 while the surface 17 of the coating is still in intimate contact with the surface 15 of the portion 14 of the lumen wall. The reopening of the spaces 19 creates a vacuum which produces a suction force (arrows 28) through the pore openings 18 on the surface, causing bodily sample material to be drawn from the portion 14 of the vessel wall through the pores and into spaces of the coating 16. The partial deflation to slightly reduced pressures may be very sudden to increase the suction force. But the balloon is deflated only a small amount so that contact with the vessel wall is maintained and the sample drawn into the polymer comes directly from the wall rather than the surrounding areas.

Figure 4:
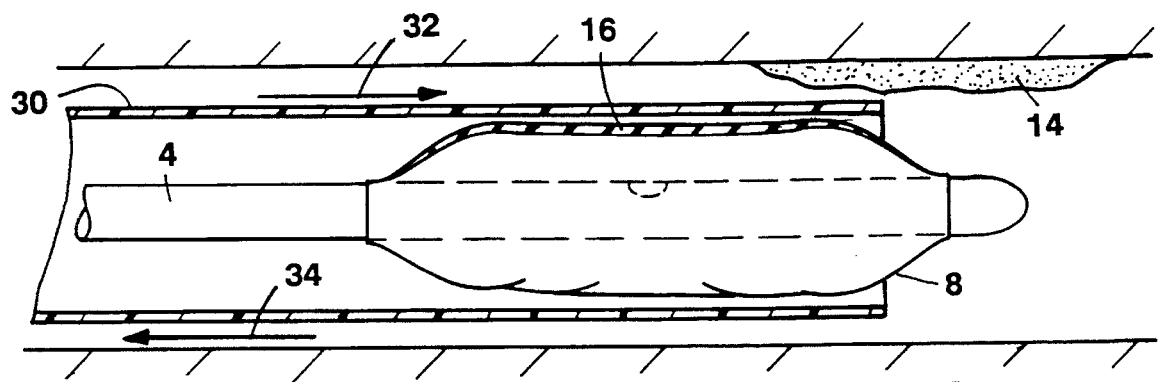

Referring to FIG. 4, with the bodily sample material collected by the coating 16, the balloon 8 is deflated to a small size. A protective sheath 30 may be slid axially (arrow 32) over the balloon, and the catheter 4 removed from the body (arrow 34). (The sheath 30 may be a guiding catheter into which the sampling catheter is drawn.)

Figure 5:
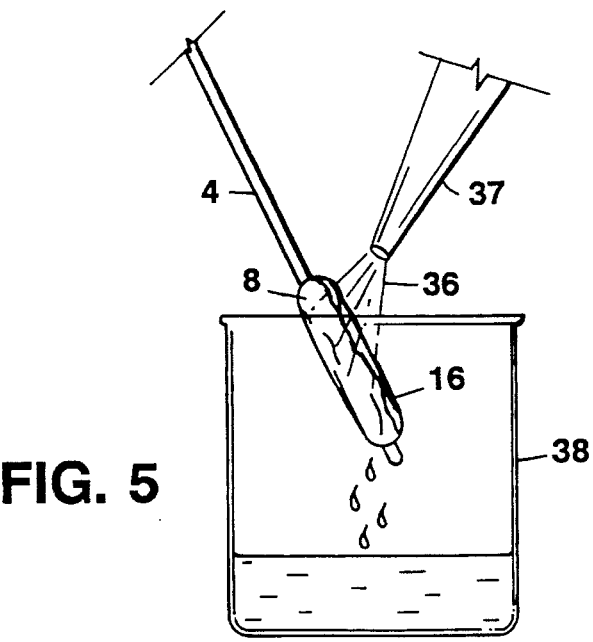
Figure 6:
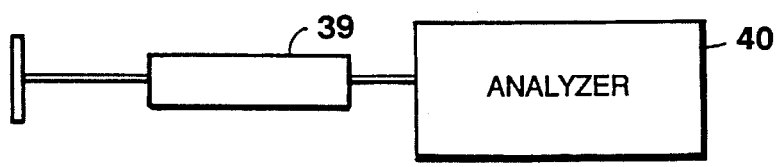

Referring to FIG. 5, outside the body, the bodily sample is removed from the coating 16 by flushing it with a liquid 36, for example, water or saline solution from a sterile flush bottle 37, which is collected in a sterile laboratory container 38. Referring to FIG. 6, a sample of the liquid is then placed in an analyzer 40 with a syringe 39. The apparatus used to recover and analyze the sample may be selected based on the type(s) of analysis to be carried out.

The coating used to collect the sample is preferably hydrophilic. It may be a cross-linked hydrogel polymer. In this case, the pores and openings are defined by the molecular matrix of the cross linked hydrogel polymer. Suitable hydrogel polymers are disclosed in Sahatjian et al., U.S. Pat. No. 5,135,516, Fan, U.S. 5,091,205, and Sahatjian "Drug Delivery System" U.S. Ser. No. 07/795,976, filed Nov. 22, 1991, now U.S. Pat. No. 5,304,121. The entire contents of all of these documents is hereby incorporated by reference. These hydrogel polymers have the ability to be compressed and expanded to create a suction force and the ability to swell to absorb bodily sample. A particular example is a polyacrylic acid hydrogel polymer of the type described in the incorporated documents having a swelled thickness of about 10–50 μm. The polymer is preswelled with saline solution before delivery into the body. The polymer is compressed against the tissue site at a low sub-dilatation pressure of about 1 to 2 atmospheres in about 0.5 minute. Partial deflation, e.g. to equilibrium pressure (no substantial force against the vessel wall) may be very rapid, in less than 10 seconds, to increase the suction force.

In embodiments, the characteristics of the polymer can be selected based on the type of bodily sample to be taken. For example, the size of the pores and spaces can be selected to collect bodily fluid samples and reject cell samples. In this case, the pores may be about 0.5 to 0.1 micron, which permits fluid to enter but prevents cells from entering. On the other hand, the pores and spaces may be selected so that cells may enter. For example, the size of the openings and spaces may be about 50 to 75 μm. In some embodiments in which the pores are too small to allow cells to pass, cell samples may nevertheless be taken in some cases because the cells can become attached to the surface by a wedging effect that occurs when cells are drawn partially into the pores.

The polymer coating need not cover the entire surface of the balloon. Rather, only a portion, e.g. one half or one third of the surface may be covered; the covered surface is then aligned with a corresponding diseased portion of the vessel wall. Several non-continuous portions of the balloon can include the polymer coating. The sections can be used to take samples from different sites in the vessel in a sequential fashion without removing the catheter from the vessel.

The polymer may also be seeded with chemical probes that preferentially retain certain bodily components. For example, DNA probes, single stranded DNA, or protein antibodies may improve the efficiency of collecting protein or DNA samples. These probes may trap DNA or RNA from genes that promote restenosis or smooth muscle cell proliferation. Radioactive marker DNA probes can be used so that subsequent analysis of the trapped DNA can be done by radiographic techniques. The probes may also be activated by heat by using a heated balloon. Chemical chelating probes can also be used that target certain chemical components, e.g., cholesterol. The probes can be cross linked into the polymer matrix, reacted with the polymer, or simply absorbed into the spaces prior to entering into the body.

Taking samples by suction force is advantageous since it is a gentle removal that effectively sloughs material, e.g. cells, fluid, from the surface and does not subject the body to the great trauma associated with severing or abraiding. In other embodiments, samples can be taken in low stress manners in which the polymer coating does not have to create a suction force or even be compressed against the tissue surface. For example, intimate contact between the polymer and tissue site can be sufficient to permit diffusional fluid exchange between the spaces in the polymer and tissue to collect material for analysis, especially when specific probes are immobilized within the polymer matrix. In another example, the balloon may also be moved slightly axially to lightly brush the coating against the surface, which gently sloughs the sample from the surface. This latter embodiment is preferably carried out with a hydrogel coating since its high lubricity, low frictional coefficient characteristics allow sample collection without excessive scraping of the surface. The sample may collect in the pore openings and may not enter the spaces in the body of the polymer. In other embodiments, the polymer is a hydrogel that is introduced into the body in the non-swelled state and positioned at a desired site. The hydrogel collects sample by absorption as it swells with body fluid at a location adjacent a desired site. In various embodiments, the polymer may be in close to but not in actual contact with the vessel wall. In embodiments, the sample is taken simultaneously with the dilation of a stenosis. In this case, the coating is provided on a dilation balloon and the balloon is inflated to dilatation pressures, e.g. 8–10 atmospheres. The invention is also applicable to areas other than the vascular system, such as the lungs or gastrointestinal tract, the urinary tract, the reproductive tract, or other parts of the body; especially those that can be accessed percutaneously by a catheter or like device.

The samples collected may be analyzed by techniques that can give a physician important information in determining or monitoring treatment. For example, a bodily sample of artherosclerotic plaque, endothelial cells, or chemical messengers, can be taken from an occluded region of an artery, particularly the coronary arteries or peripheral vessels, and analyzed to determine whether an injury has occured and, also the nature of the injury. For example, the analysis can determine whether the occlusion is highly calcified, or highly cholesteric, or highly fibrotic. These types of lesions may be differentiated based on cell samples or chemical indicators such as enzymes or proteins that are precursors to, for example, proliferation. DNA and RNA samples may as well be analyzed to the same effect. Analyses may be done by visual inspection, chemical analyses or spectral analyses, and by using methods such as gel permeation chromatography, infrared spectroscopy, electrophoresis, and micro analytical techniques. For example, plaque recognition by laser excited fluorescence spectroscopy is discussed by Bertorelli et al., *JACC*, Vol. 17, No. 6, May 1991, p. 160B, which is incorporated by reference. In some cases, the type of sample may be determined by visual observation by a physician. An example is a highly calcified sample. The sample, particularly cells, can also be analyzed for malignancy.

This information can determine what course of treatment should be followed. For example, if the sample is highly calcified, a laser ablation treatment may be the most effective in removing the occlusion. If highly cholesteric, a cholesterol dissolving drug may be delivered to the site or systemically. If highly fibrotic, an antiproliferative drug may be delivered. Another possible treatment is gene therapy including the delivery of antisense biochemical drugs. Gene therapy is discussed, for example, in Nabel et al., *JACC*, Vol. 17, No. 6, May 1991, 189B-94B, the entire contents of which is hereby incorporated by reference. A drug delivery system is described in U.S. Ser. No. 07/795,976, incorporated supra. Drug delivery is also discussed in Wang U.S. Pat. No. 5,254,089, the entire contents of which is hereby incorporated by reference.

In cases where cells are obtained using the methods and devices described above, in addition to or instead of analysis, the cells may be cultured outside the body and then placed back into the patient. For example, the cells may be introduced back into the patient as an autologous coating on a graft or stent. The cells may also be placed back into the body using the device described above by disposing them on or in the coating outside the body, delivering the device to position the coating at a desired site inside the body, then releasing the cells from the coating, e.g., by squeezing them out of the coating by compressing the coating against the site in a manner similar to drug delivery discussed in U.S. Pat. No. 5,304,121, supra. The cells may also be altered, e.g. genetically, before placing them back into the body.

Another technique for collecting samples is discussed in a pending application filed on the same day as this application by Sahatjian, Ronald A. entitled "Sample Collection" U.S. Ser. No. 08/175,949, filed Dec. 30, 1993, now U.S. Pat. No. 5,409,012; the entire contents of this application is incorporated/herein by reference.

Still further embodiments are within the following claims. For example, the methods and apparatus described above can be constructed and adapted for taking samples from parts of the body other than the vascular system. The coating may be used on a catheter without an expandable balloon.

What is claimed is:

1. A method for taking a bodily sample from a blood vessel of a patient and collecting said sample outside the body, comprising:

providing a sampling probe in the form of an elongate vascular catheter having a proximal portion that remains outside the body and a distal portion that can be located in the blood vessel, said distal portion including an expandable portion that can be selectively expanded to larger diameters and contracted to smaller diameters, said expandable portion including a polymer on its outer surface capable of receiving a substantial amount of bodily sample suitable for detecting disease or monitoring a treatment, positioning said expandable portion at a desired location within said blood vessel, and taking said sample by expanding said expandable portion to contact the wall Of said blood vessel with said polymer with sufficient force to compress said polymer to a reduced thickness, contracting said expandable portion to re-expand said polymer and draw said sample into said polymer by suction forces created by said re-expansion, further contracting said expandable portion to smaller diameter so that said polymer does not contact said wall of said blood vessel, removing said catheter from said patient, collecting said sample outside the body, and analyzing said sample to detect disease or monitor said treatment.

2. The method of claim 1 wherein said polymer is a hydrogel.

3. The method of claim 2 wherein said vascular catheter is in the form of an angioplasty catheter, said expandable portion being in the form of an inflatable balloon, said hydrogel being disposed as a coating over said balloon.

4. The method of claim 3 comprising:

positioning said expandable portion adjacent an occlusion in said vessel, expanding said occlusion and collecting said sample by said contacting of said expandable portion.

5. The method of claim 3 comprising:

performing angioplasty on region of the blood vessel having an occlusion, after angioplasty, positioning the expandable portion adjacent to the region, and collecting the sample from the region.

6. The method of claim 1 comprising:

removing said sample from said polymer prior to said analyzing.

7. The method of claim 1 comprising:

removing said sample by flushing said polymer with aqueous solution.

8. The method of claim 1, wherein said polymer includes a chemical probe for preferentially binding a target component.

9. A method for taking a bodily sample from a blood vessel of a patient and collecting said sample outside the body, comprising:

providing a sampling probe in the form of an elongate vascular catheter having a proximal portion that remains outside the body and a distal portion that can be located in the blood vessel, said distal portion including an expandable portion that can be selectively expanded to larger diameters and contracted to smaller diameters, said expandable portion including a hydrogel on its outer surface capable of receiving a substantial amount of bodily sample suitable for detecting disease or monitoring a treatment, positioning said expandable portion at a desired location within said blood vessel, and taking said sample by exposing said hydrogel by expanding said expandable portion sufficient to place said hydrogel in proximity with the wall of said blood vessel so that said bodily sample is received by said hydrogel, contracting said expandable portion to a smaller diameter so that said hydrogel does not contact said wall of said blood vessel, removing said catheter from said patient, collecting said sample outside the body, and analyzing said sample to detect disease or monitor said treatment.

10. The method of claim 9 comprising:

introducing said catheter into said blood vessel while said hydrogel is in a substantially nonswelled state, and collecting said sample by absorption into said hydrogel as said hydrogel swells during exposure.

11. The method of claim 10 comprising:

providing a sheath that can be positioned over said expandable portion to limit exposure of said hydrogel prior to positioning at said desired location, and exposing said expandable portion from said sheath after positioning at said desired location.

12. The method of claims 2 or 11 comprising:

providing a sheath that can be positioned over said expandable portion after collecting said sample to reduce exposure of said hydrogel while removing said catheter from said patient.

13. The method of claim 9 comprising:

introducing said catheter into said blood vessel while said hydrogel is in a substantially nonswelled state, and collecting said sample by absorption into said hydrogel as said hydrogel swells during exposure.

14. The method of claim 13 comprising:

providing a sheath that can be positioned over said expandable portion to limit exposure of said hydrogel prior to positioning at said desired location, and exposing said expandable portion from said sheath after positioning at said desired location.

15. The method of claims 14 comprising:

providing a sheath that can be positioned over said expandable portion after collecting said sample to reduce exposure of said hydrogel while removing said catheter from said patient.

16. The method of claim 9, wherein said vascular catheter is in the form of an angioplasty catheter, said expandable portion being in the form of an inflatable balloon, said hydrogel being disposed as a coating over said balloon.

17. The method of claim 16 comprising:

positioning said expandable portion adjacent an occlusion in said vessel, simultaneously expanding said occlusion and collecting said sample by expanding said expandable portion.

18. The method of claim 16 comprising:

performing angioplasty on a region of the blood vessel having an occlusion, after angioplasty, positioning the expandable portion adjacent to the region, and collecting the sample from the region.

19. The method of claim 9 comprising:

removing said sample from said hydrogel prior to said analyzing.

20. The method of claim 19 comprising:

removing said sample by flushing said hydrogel with aqueous solution.

21. The method of claim 9 comprising:

moving said catheter axially while said hydrogel is in contact with said wall of said vessel to brush said hydrogel along said wall to collect said sample, wherein said sample is taken without excessive mechanical disturbance to said wall of said blood vessel.

22. The method of claim 9, wherein said hydrogel includes a chemical probe for preferentially binding a target component.

23. A method for treating a patient by taking a bodily tissue sample from deep within the body of a patient and collecting said sample outside the body to facilitate treatment of the patient, comprising:

providing a sampling probe in the form of an elongate catheter having a proximal portion that remains outside the body and a distal portion that can be located within the body, said distal portion including an expandable portion that can be selectively expanded to larger diameters and contracted to smaller diameters, said expandable portion including a polymer on its outer surface capable of receiving a substantial amount of said sample suitable for detecting disease or monitoring a treatment, positioning said catheter within the body, and taking said sample by expanding said expandable portion to contact said bodily tissue with said polymer with sufficient force to compress said polymer to a reduced thickness, contracting said expandable portion to re-expand said polymer and draw said sample into said polymer by suction forces created by said re-expansion, removing said catheter from said patient, collecting said sample outside the body, and analyzing said sample to detect disease or monitor said treatment.

24. The method of claim 23 wherein said polymer is a hydrogel.

25. A method for treating a patient by taking a bodily tissue sample from deep within the body of a patient and collecting said sample outside the body to facilitate treatment of the patient, comprising:

providing a sampling probe in the form of an elongate vascular catheter having a proximal portion that remains outside the body and a distal portion that can be located within the body, said distal portion including an expandable portion that can be selectively expanded to larger diameters and contracted to smaller diameters, said expandable portion including a hydrogel on its outer surface capable of receiving a substantial amount of bodily sample suitable for detecting disease or monitoring a treatment, positioning said expandable portion at a desired location within the body, and taking said sample by exposing said hydrogel by expanding said expandable portion sufficient to place said hydrogel in proximity with said bodily tissue so that said bodily sample is received by said hydrogel, contracting said expandable portion to a smaller diameter so that said hydrogel does not contact said bodily tissue, removing said catheter from said patient, collecting said sample outside the body, and analyzing said sample to detect disease or monitor said treatment.

* * * * *